US012672892B2

(12) United States Patent
Artes et al.

(10) Patent No.: US 12,672,892 B2
(45) Date of Patent: Jul. 7, 2026

(54) PROBE

(71) Applicant: Erbe Elektromedizin GmbH,
Tuebingen (DE)

(72) Inventors: Charlotte Artes, Bodelshausen (DE);
Waldemar Wandel, Kusterdingen (DE)

(73) Assignee: ERBE ELEKTROMEDIZIN GMBH,
Tuebingen (DE)

( * ) Notice: Subject to any disclaimer, the term of this
patent is extended or adjusted under 35
U.S.C. 154(b) by 788 days.

(21) Appl. No.: 17/095,948

(22) Filed: Nov. 12, 2020

(65) Prior Publication Data

US 2021/0153887 A1      May 27, 2021

(30) Foreign Application Priority Data

Nov. 22, 2019   (EP) ..................................... 19210911

(51) Int. Cl.
A61B 18/00      (2006.01)
A61B 17/3203      (2006.01)
A61B 18/14      (2006.01)

(52) U.S. Cl.
CPC ...... A61B 17/3203 (2013.01); A61B 18/1477
(2013.01); *A61B 2018/1405* (2013.01); *A61B*
*2018/1475* (2013.01)

(58) Field of Classification Search
CPC .. A61B 2018/1475; A61B 2018/00196; A61B
17/3203; A61B 2017/00367; A61B
2017/0038; A61B 2017/2919; A61B
2018/00958; A61B 2018/00946; A61B 18/14; A61B 18/1477; A61B 17/32037;
A61B 2017/32032; A61B 2017/32035;
A61M 25/0136; A61M 25/0147
See application file for complete search history.

(56) References Cited

U.S. PATENT DOCUMENTS

| | | | | |
|---|---|---|---|---|
| 3,262,427 | A | * | 7/1966 | Von Arx Marcel .. B43K 24/163 |
| | | | | 401/31 |
| 4,811,733 | A | | 3/1989 | Borsanyi et al. |
| 5,449,356 | A | | 9/1995 | Walbrink et al. |
| 5,685,877 | A | * | 11/1997 | Pagedas ............. A61B 18/1482 |
| | | | | 606/41 |
| 5,697,281 | A | | 12/1997 | Eggers et al. |
| 6,033,404 | A | * | 3/2000 | Melzer ............... A61B 18/1482 |
| | | | | 606/41 |
| 6,171,277 | B1 | * | 1/2001 | Ponzi ................ A61M 25/0147 |
| | | | | 604/95.04 |

(Continued)

FOREIGN PATENT DOCUMENTS

| | | |
|---|---|---|
| CN | 1678249 A | 10/2005 |
| CN | 1771888 A | 5/2006 |

(Continued)

*Primary Examiner* — Linda C Dvorak
*Assistant Examiner* — Davina E. Lee
(74) *Attorney, Agent, or Firm* — Blank Rome LLP

(57)      ABSTRACT
A probe for electrosurgical treatment of tissue. An electrode
is movably arranged in an extension direction of an elec-
trode channel inside a probe body. The probe body is
connected with an operating device at the proximal end. The
operating device comprises an electrode operating element
to shift the electrode along the electrode channel. The
movement coupling between the electrode operating ele-
ment and the electrode is established via a reduction gear, for
example a lever gear.

14 Claims, 10 Drawing Sheets

(56)  References Cited

U.S. PATENT DOCUMENTS

| | | | |
|---|---|---|---|
| 6,607,529 B1 | 8/2003 | Jones et al. | |
| 7,507,232 B1 | 3/2009 | Garito et al. | |
| 7,815,638 B2 | 10/2010 | Farin et al. | |
| 8,216,234 B2 | 7/2012 | Long | |
| 8,814,856 B2 * | 8/2014 | Elmouelhi | A61B 18/1492 |
| | | | 606/41 |
| 9,138,251 B2 | 9/2015 | Kuehner et al. | |
| 9,579,090 B1 * | 2/2017 | Simms | A61B 17/00234 |
| 9,622,768 B2 | 4/2017 | Fischer et al. | |
| 9,872,727 B2 | 1/2018 | Motai | |
| 10,080,605 B2 | 9/2018 | Nutting | |
| 2002/0095176 A1 * | 7/2002 | Prestel | A61B 10/06 |
| | | | 606/205 |
| 2002/0169362 A1 | 11/2002 | Kan et al. | |
| 2005/0288664 A1 | 12/2005 | Ford et al. | |
| 2007/0149968 A1 * | 6/2007 | Gonon | A61B 17/3203 |
| | | | 606/49 |
| 2008/0269862 A1 | 10/2008 | Elmouelhi et al. | |
| 2012/0078244 A1 | 3/2012 | Worrell et al. | |
| 2013/0131666 A1 | 5/2013 | Atwell et al. | |
| 2013/0158544 A1 | 6/2013 | Kuhner et al. | |
| 2013/0231611 A1 | 9/2013 | Lischinsky et al. | |
| 2015/0073394 A1 | 3/2015 | Schiele | |
| 2015/0088130 A1 * | 3/2015 | Sekino | A61B 17/3203 |
| | | | 606/46 |
| 2015/0238217 A1 * | 8/2015 | Uchida | A61B 17/3203 |
| | | | 606/167 |
| 2015/0238225 A1 * | 8/2015 | Sekino | A61B 18/1482 |
| | | | 606/46 |
| 2015/0335376 A1 | 11/2015 | Hufnagel et al. | |
| 2015/0335377 A1 | 11/2015 | Brooke | |
| 2016/0074097 A1 | 3/2016 | Nutting | |
| 2017/0296388 A1 * | 10/2017 | Gaynes | A61B 1/018 |
| 2019/0328399 A1 | 10/2019 | Baril et al. | |
| 2019/0328451 A1 * | 10/2019 | Smith | A61M 5/162 |

FOREIGN PATENT DOCUMENTS

| | | | |
|---|---|---|---|
| CN | 101579256 A | 11/2009 | |
| CN | 101983038 A | 3/2011 | |
| CN | 102647949 A | 8/2012 | |
| CN | 103156680 A | 6/2013 | |
| CN | 103356281 A | 10/2013 | |
| CN | 104203139 A | 12/2014 | |
| CN | 104434265 A | 3/2015 | |
| CN | 105286987 A | 2/2016 | |
| CN | 106510842 A | 3/2017 | |
| CN | 106955159 A | 7/2017 | |
| CN | 108354664 A | 8/2018 | |
| CN | 209091618 U | 7/2019 | |
| EP | 2485661 B1 | 10/2013 | |
| JP | H11164835 A | 6/1999 | |
| JP | 2000262527 A | 9/2000 | |
| JP | 2005204995 A | 8/2005 | |
| JP | 2005261698 A | 9/2005 | |
| JP | 2013106949 A | 6/2013 | |
| JP | 201558233 A | 3/2015 | |
| JP | 2015159924 A | 9/2015 | |
| JP | 2017176584 A | 10/2017 | |
| RU | 2008133567 A | 2/2010 | |
| RU | 2013118694 A | 10/2014 | |
| WO | 2015056624 A1 | 4/2015 | |

* cited by examiner

PROBE

CROSS REFERENCE TO RELATED APPLICATION

This application claims the benefit of European Application No. 19210911.4, filed Nov. 22, 2019, the subject matter of which is incorporated by reference herein in its entirety.

TECHNICAL FIELD

Embodiments of the invention refer to a probe for electrosurgical treatment of tissue. The probe has a probe body with an electrode movably arranged therein. The probe can be a monopolar probe with one single electrode or a bipolar probe with multiple electrodes. By means of an operating device the electrode can be extended from the probe body or retracted into the probe body. In the extended condition voltage can be applied to the electrode, particularly for cutting of tissue.

BACKGROUND

Such probes are known from practice. For a surgeon the requirement exists to exactly adjust the length of the distal end section of the electrode moved out of the probe body. In so doing, it can be avoided that the electrode penetrates into deeper tissue layers during cutting of tissue that shall not be cut or damaged during the intervention.

SUMMARY

Thus, it is the object of embodiments of the present invention to provide a probe that allows improved handling for a surgeon.

This object is solved with a probe according to claim 1.

Embodiments of the inventive probe are configured for electrosurgical treatment of tissue and comprise a probe body in which an electrode channel extends up to the distal end of the probe body. At the proximal end the probe body is connected with an operating device. The probe body can be configured as rigid tube or preferably as flexible hose. A rigid tube means a probe body that cannot be bent under the forces that usually occur during the use of the probe. In turn a flexible hose means a probe body that can be bent compared with its initial extension direction during the correct use of the probe under the usually occurring forces. A probe with a flexible hose as probe body can be, for example, guided through an endoscope channel of an endoscope.

The operating device has a housing. On the housing an electrode operating element is arranged. The electrode operating element is movable between a first position and a second position, e.g. linearly shiftable. As an alternative the electrode operating element can also be pivotably arranged on the housing between the first position and the section position.

An electrode is arranged in the electrode channel of the probe body that is movably supported along the extension direction of the electrode channel. The distal end of the electrode can be moved between a fully extended position and a fully retracted position. In the fully extended position a distal end section adjoining the distal end of the electrode located outside of the electrode channel is longest. In the fully retracted position the distal end of the electrode is located inside the electrode channel.

The electrode operating element of the operating device serves for retracting and extending the electrode. The electrode operating element is movably coupled with the electrode by a reduction gear. The reduction gear is configured to reduce a movement of the electrode operating element in a shorter movement of the electrode according to the reduction ratio. This means that an operating path of the electrode operating element is longer than the path that the electrode travels, if the electrode operating element is moved along the operating path. Particularly the maximum provided operating path between the first position and the section position is longer than the path the electrode moves between the fully extended position and the fully retracted position. The reduction of the reduction gear is preferably constant and does not depend on the position or traveled path.

Due to the reduction, the surgeon can achieve very accurate positioning of the electrode by means of a long operating path of the electrode operating element. In doing so, the distal end of the electrode can be simply and exactly positioned, particularly with an accuracy in the sub-millimeter range.

It is advantageous, if the reduction gear is a lever gear. In an embodiment the lever gear can comprise a lever that is pivotably supported at a pivot location on the housing of the operating device. Preferably the lever gear has only one single lever. A coupling location, at which the electrode operating element is coupled with the lever, is farther away from the pivot location than a coupling location at which the lever is coupled with the electrode. In this manner a simply configured lever gear with a reduction is achieved.

The pivot location can be arranged at one end of the lever.

In one embodiment the coupling location of the electrode with the lever is located between the pivot location and the coupling location at which the electrode operating element engages the lever.

Instead of a lever gear also other gear types can be used, such as an eccentric gear, a gear with a toothed rack and a toothed wheel, a toothed wheel gear, a belt gear, a friction wheel gear, etc. Also combinations of the described gear types are possible. The reduction gear can have one or more gear stages.

In another advantageous configuration that can be particularly realized also independent from the reduction gear, the probe comprises a latch device. The latch device can define multiple different positions of the electrode relative to the probe body. Particularly the latch device can define these positions by a latched position in each case. Due to the latched positions of the latch device, defined pre-specified positions of the electrode and particularly the distance of the distal end of the electrode from the distal end of the probe body can be exactly adjusted such that the positioning of the electrode is simplified for the surgeon.

In one embodiment the latch device defines a fully extended position of the electrode, a fully retracted position of the electrode and at least one intermediate position of the electrode between the fully extended position and the fully retracted position.

In a preferred embodiment the latch device has a latch element movably coupled with the electrode operating element and a latch counter element movably coupled with the housing of the operating device. Preferably the latch counter element is immovably arranged relative to the electrode operating element. Preferably the latch counter element is immovably arranged relative to the housing. In each pre-specified defined position of the electrode relative to the probe body the latch element and the latch counter element take a latched position in which a releasable latched connection is established between the latch element and the latch counter element.

The latch element can comprise at least one latch projection and/or at least one latch recess. The latch counter element can comprise at least one latch recess and/or at least one latch projection for cooperation with the latch element. For example, one single latch projection can be provided that engages in one assigned latch recess in each case in the different defined positions of the electrode. Conversely, one single latch recess can be present in which one of multiple latch elements engages in the different defined positions of the electrode in each case. Also, in each latched position—when the releasable latch connection is established—multiple latch projections can engage into multiple assigned latch recesses.

In all of the described embodiments the latch projection can be elastically movably supported, for example, such that the latch projection allows a relative movement of the electrode operating element relative to the housing of the operating device out of a latched position. For example, an elastically or spring elastically biased ball or another body can form a latch projection that—due to the spring bias—engages a depression or hole that forms a latch recess. The latch projection can be biased by a spring or also an elastically deformable element and can be movably supported counter to the biasing force, e.g. by means of a kind of film hinge.

In a preferred embodiment the probe comprises a biasing device. The biasing device applies a biasing force on the electrode relative to the probe body in the extension direction of the electrode or the electrode channel. The biasing device can have one or multiple biasing elements, particularly at least one spring and preferably a helical spring. Due to the biasing force, a movement play of the electrode in extension direction can be eliminated.

It is preferred, if the biasing force of the biasing device urges the electrode in direction toward the fully extended position.

It is particularly also advantageous, if the biasing force has an amount that is larger than the counter force applied during cutting of tissue on the electrode during use of the probe.

In a preferred embodiment the biasing device or at least one biasing element of the biasing device is arranged in the probe body or in the electrode channel and can be supported, for example, at the probe body on one side and at the electrode on the other side. Preferably the biasing device or at least one biasing element is distally arranged, particularly either directly behind a distal end piece of the probe body or with a distance of, e.g. 10-15 cm away from the end piece, i.e. displaced back proximally so-to-speak. Due to such a distance, a clamping of the biasing device or of the at least one biasing element can be avoided during bending of the probe body or an endoscope in the distal end region.

Alternatively or additionally, the biasing device or at least one biasing element of the biasing device can be arranged in the housing of the operating device.

The probe can be configured as combined probe or hybrid probe. In this embodiment the probe comprises a water jet probe body in addition to the electrode in which a water channel extends up to the distal end of the water jet probe body. The water jet probe body extends, for example, substantially parallel to the probe body with the electrode channel. The probe body that comprises the electrode channel and that can be referenced to as electrode probe body can be arranged in an outer body, e.g. an outer tube or an outer hose, together with the water jet probe body. Analog to the probe body the water jet probe body and/or the outer body can be configured in the form of a rigid tube or a flexible hose respectively. In an embodiment the probe body comprising the electrode channel can also form the outer body in which the channel for the water jet probe body is provided.

In such a combined probe or hybrid probe the water jet probe body can be shiftably arranged along its extension direction relative to the housing of the operating device and/or an outer body. The operating device is particularly configured to allow a movement of the water jet probe body in direction toward an extended position only in the case, if the electrode is located distant from the fully extended position or if the electrode is located in the completely retracted position. This can be achieved in that the water jet probe body can only be extended by means of the operating device concurrently with retracting the electrode or can alternatively be extended only when the electrode is partly or fully retracted. This aspect of the configuration of the combined probe or hybrid probe can also be implemented independent from how the electrode operating device is movably coupled with the electrode, this is particularly independent from whether a reduction gear is present or not as well as independent from the presence of a latch device.

In one embodiment the operating device comprises a water jet probe operating element. The water jet probe operating element is configured to move or shift the water jet probe body in the extension direction relative to the housing. The water jet probe operating element is arranged at the housing of the operating device and can be formed by a slider, for example.

The electrode operating element and the water jet probe operating element can be arranged adjacent to each other at the housing such that in the first position the electrode operating element forms a stop for the water jet probe operating element. According to the example, the electrode is fully extended in the first position of the electrode operating element. In this first position the water jet probe operating element cannot be moved. The movement of the water jet probe operating element is preferably blocked in one direction by the housing and in the other direction by the electrode operating element taking the first position. The extension of the water jet probe body is thus impeded, if the electrode is operated.

In another preferred embodiment the electrode operating element can be configured for movement of the electrode as well as for movement of the water jet probe body. In this embodiment the electrode operating element is movably coupled with the electrode as well as with the water jet probe body.

It is advantageous, if the electrode operating element is configured to first effect a retraction movement of the electrode during a movement out of the first position in direction toward the second position. Only after the start of the retraction movement or after reaching the fully retracted position of the electrode, an extension movement of the water jet probe body is effected by a continued movement of the electrode operating element away from the first position. Thus, the electrode operating element is only able to move the electrode in a first movement section directly adjoining the first position. In a movement section that directly adjoins the second position, the electrode operating element is only able to effect a movement of the water jet probe body. The two movement sections can have a spatial distance, can adjoin each other directly or can partly overlap.

It is also advantageous, if a deflection device is present in the housing that is configured to couple the water jet probe body with the assigned operating element of the operating device such that the movement directions of the water jet probe body located outside the housing and the operating element are opposed to each other. For example, the water jet probe body can be deflected by a deflection device within the housing. Preferably the deflection device deflects the water jet probe body approximately about 180° such that it has a U-shaped form in the area of the deflection device. Due to the deflection, the sections of the water jet probe body adjacent to the deflection device are moved in opposite directions. In doing so, the possibility is provided that due to a movement of the proximal end of the water jet probe body in one direction, a movement of the water jet probe body arranged outside the housing and, e.g. of the distal end of the water jet probe body in the opposite direction, is achieved.

BRIEF DESCRIPTION OF THE DRAWINGS

Preferred embodiments of the invention may be captured, for example, in dependent claims, the description and the drawings. In the following, embodiments of the invention are explained with reference to the attached drawings. The drawings show:

DETAILED DESCRIPTION

Figure 1:
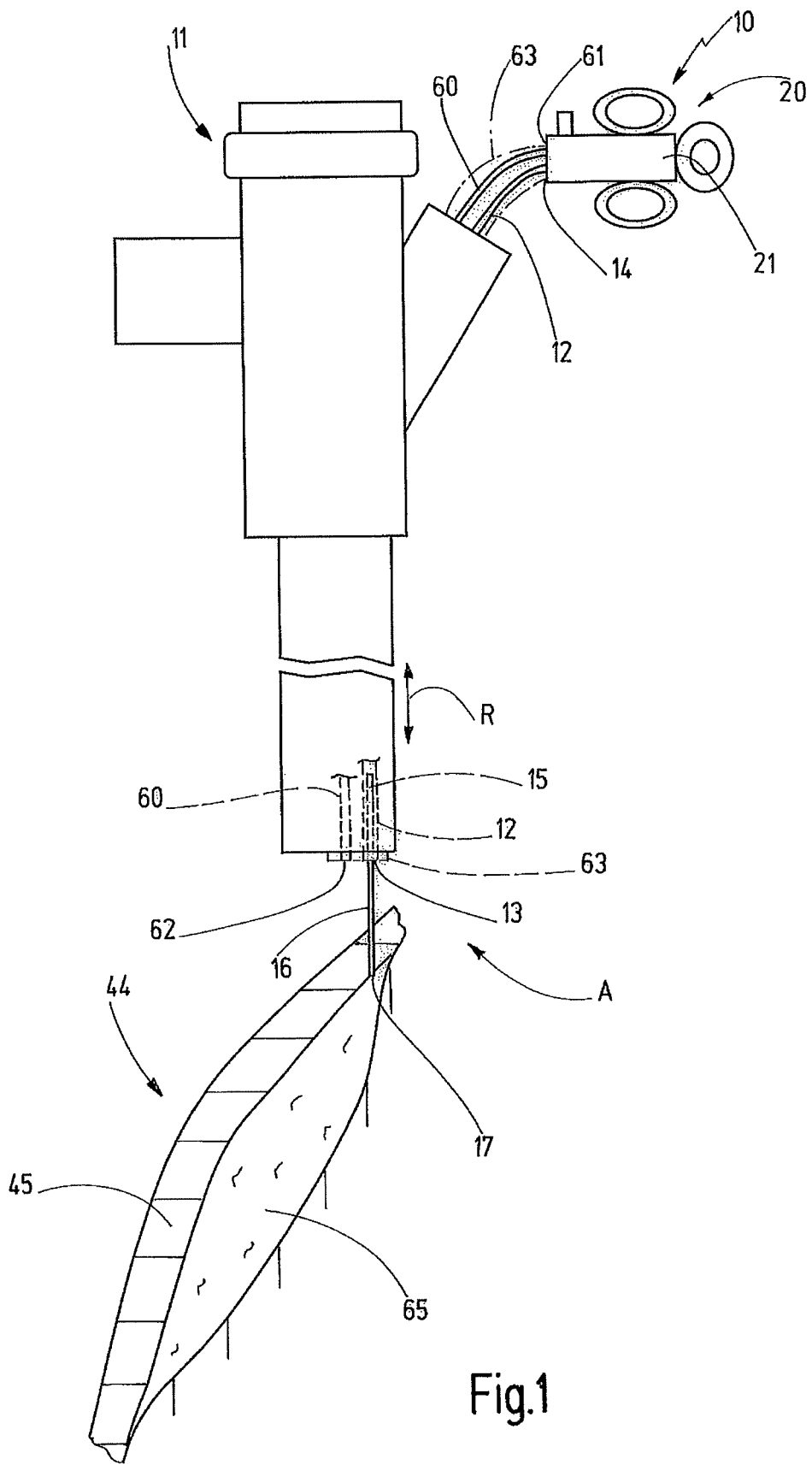
FIG. 1 a schematic block-diagram-like illustration of an embodiment of a probe with extended electrode and retracted water jet probe body, FIG. 2 a schematic block-diagram-like basic illustration of an operating device of the probe of FIG. 1 having an electrode operating element that is in a first position, FIG. 3 the operating device of FIG. 2, wherein the electrode operating element is in a second position, FIG. 4 the operating device according to FIGS. 2 and 3 in a modified embodiment, wherein the electrode operating element is in a first position, FIGS. 5 to 7 a schematic basic illustration of a deflection device respectively for the operation or movement of the water jet probe body of the probe, FIG. 8 a schematic basic illustration of an operating device of a probe having a latch device, FIG. 9 a perspective partial illustration of an embodiment of a housing of an operating device of a probe having a latch device, FIGS. 10 to 12 a respective basic illustration of a further embodiment of an operating device having an electrode operating element that is configured for movement of the electrode as well as the water jet probe body in different positions, FIG. 13 a schematic basic illustration of a coupling device of the operating device according to FIGS. 10 to 12, FIG. 14 a schematic basic illustration of a coupling body that is connected with the proximal end of the electrode, FIG. 15 a distal end section of the electrode as well as the probe body in a fully extended position of the electrode comprising a biasing device arranged in the probe body, FIG. 16 the arrangement of FIG. 15 with fully retracted electrode, FIG. 17 a modified embodiment of the probe body, wherein the biasing device is arranged farther away from the distal end of the probe body, FIG. 18 a schematic basic illustration of a stop for the distal end of the electrode in an end piece of the probe body that comprises a depression according to the example in which the distal end of the electrode can engage at least partly, FIG. 19 a basic illustration of an embodiment of an operating device in side view, wherein the water jet probe can be, e.g. moved by a pressure element, FIG. 20 another embodiment of an operating device in a partly cut perspective view and FIG. 21 an embodiment of a rotary mechanism of an operating device.

Probe 10 is schematically illustrated in FIG. 1 that is used in combination with an endoscope 11. The probe 10 is configured as combined probe and comprises a probe body 12 that has a distal end 13 as well as a proximal end 14. An electrode channel 15 (FIGS. 15-17) in which an electrode 16 is shiftably arranged in an extension direction R of the electrode channel 15, is arranged inside the probe body 12. The electrode 16 can be moved out of the probe body 12 up to a fully extended position A (FIGS. 1, 15, 17, 18), wherein a distal end 17 of the electrode 16 has the longest distance to the distal end 13 of the probe body 12 in the fully extended position A. In a fully retracted position E (FIG. 16), preferably the electrode 16 is arranged inside the probe body 12 and the distal end 17 of the electrode 16 is arranged in the area of the distal end 13 of the probe body 12. In a modified embodiment the distal end 17 can also slightly project out of the electrode channel 15 or the probe body 12 in the fully retracted position E.

The probe body 12 can be configured as rigid tube or, as in the present embodiment, as flexible hose. In the configuration in form of a flexible hose the probe body 12 is resiliently bendable with the usual forces occurring during use and can be particularly used in combination with an endoscope 11, as illustrated in FIG. 1.

At the proximal end 14 the probe body 12 is connected with an operating device 20. The operating device 20 has a housing 21. According to the example, the probe body 12 can be attached to the housing 21 and can be open to an inner space of the housing 21. A proximal end section 22 of the electrode 16 can be guided out of the electrode channel 15 or the probe body 12 in the inner space of the housing 21.

On the housing 21 an electrode operating element is movably and according to the example shiftably arranged. The electrode operating element 23 has two engagement openings 24 according to the example, in order to grip it with two fingers and to shift it along the housing 21 according to the example.

For movement of the electrode 16 between the fully extended position A and the fully retracted position E the electrode operating element 23 can be moved or shifted between a first position I (FIGS. 2 and 4) and a second position II. The electrode operating element 23 is movably coupled with the electrode 16. In the first position I the electrode 16 takes the fully extended position A and in the second position II the electrode 16 takes the fully retracted position E.

Figures 2, 3:
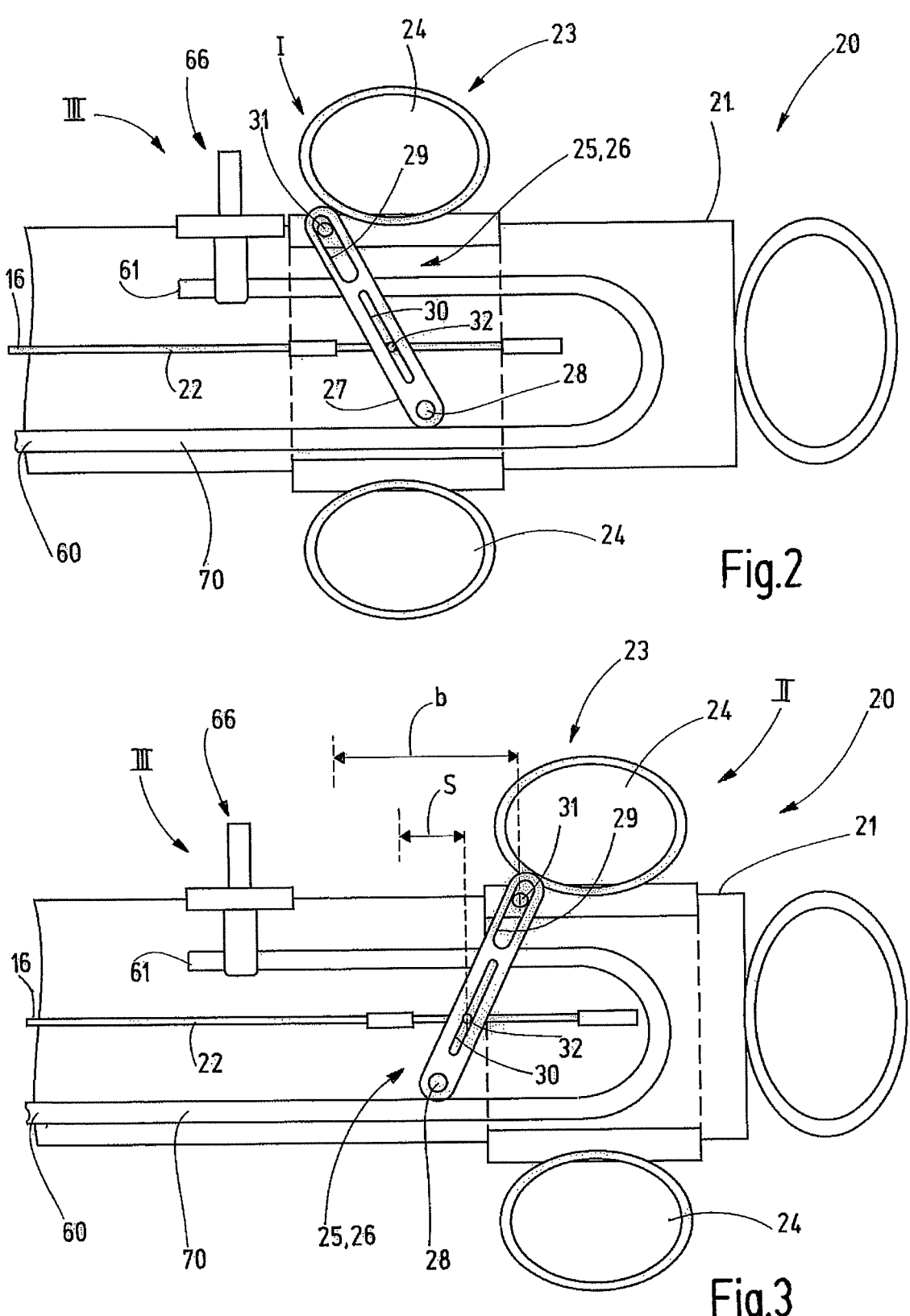

In an embodiment according to the invention of the probe 10 or the operating device 20, the electrode operating element 23 is movably coupled with the electrode 16 by a reduction gear 25. The reduction gear 25 is configured such that a traveled operating path b of the electrode operating element 23 is longer than a path s the electrode 16 travels in extension direction R. In FIG. 3 the maximum provided operating path b between the first position I and the second position II and the path s traveled by the electrode 16 thereby are illustrated.

It is noted here that the drawings are only basic illustrations and that they do not form illustrations to scale. Particularly the reduction ratio of the reduction gear 25 can have a different reduction ratio than symbolized schematically in FIG. 3 by the operating path b and the path s.

In the preferred embodiment the reduction gear 25 is configured as lever gear 26, particularly as one-arm lever gear 26. The lever gear 26 has one and preferably exactly one lever 27 that is pivotably arranged on the housing 21 at a pivot location 28. The pivot axis is thereby arranged orthogonal to the movement direction of the electrode operating element 23.

A first groove 29 as well as a second groove 30 are provided in the lever 27 with distance to the pivot location 28. A first sliding block 31 extends in the first groove 29 that is arranged at the electrode operating element 23 immovably relative to the electrode operating element 23. A second sliding block 32 engages in the second groove 30 that is arranged at the proximal end section 22 immovably relative to the proximal end section 22 of the electrode 16. The two grooves 29, 30 extend parallel to each other and according to the example, in a straight line respectively and preferably along a common straight line that can extend through the pivot location 28. The second groove 30 is located between the first groove 29 and the pivot location 28 according to the example. The second sliding block 32 is shiftably arranged along the second groove 30 and the first sliding block 31 is shiftably arranged along the first groove 29.

Alternatively to this configuration with two separate grooves 29, 30 also a common groove for the two sliding blocks 31, 32 could be provided. Thus, at least one groove is present.

During a movement of the electrode operating element along the operating path b between the first position I and the second position II the lever 27 is pivoted about the pivot location 28. The position of the first sliding block 31 in the first groove 29 corresponds to a coupling location between the electrode operating element 23 and the reduction gear 25 or the lever gear 26. The position of the second sliding block 32 in the second groove 30 corresponds to a coupling location between the electrode 16 or the proximal end section 22 and the reduction gear 25 or the lever gear 26. Because this latter coupling position is arranged closer to the pivot location 28, a reduction is effected by the lever gear 26, whereby it applies: The operating path b is longer than the path s.

Preferably the pivot location 28 is provided at one end of the lever 27 as illustrated in the drawings. In modification hereto the pivot location 28 could also be arranged between the first groove 29 and the second groove 30, wherein the distance of the sliding blocks 31, 32 is selected such that a reduction of the operating movement into the shifting movement of the electrode 16 is achieved.

Figures 20, 21:
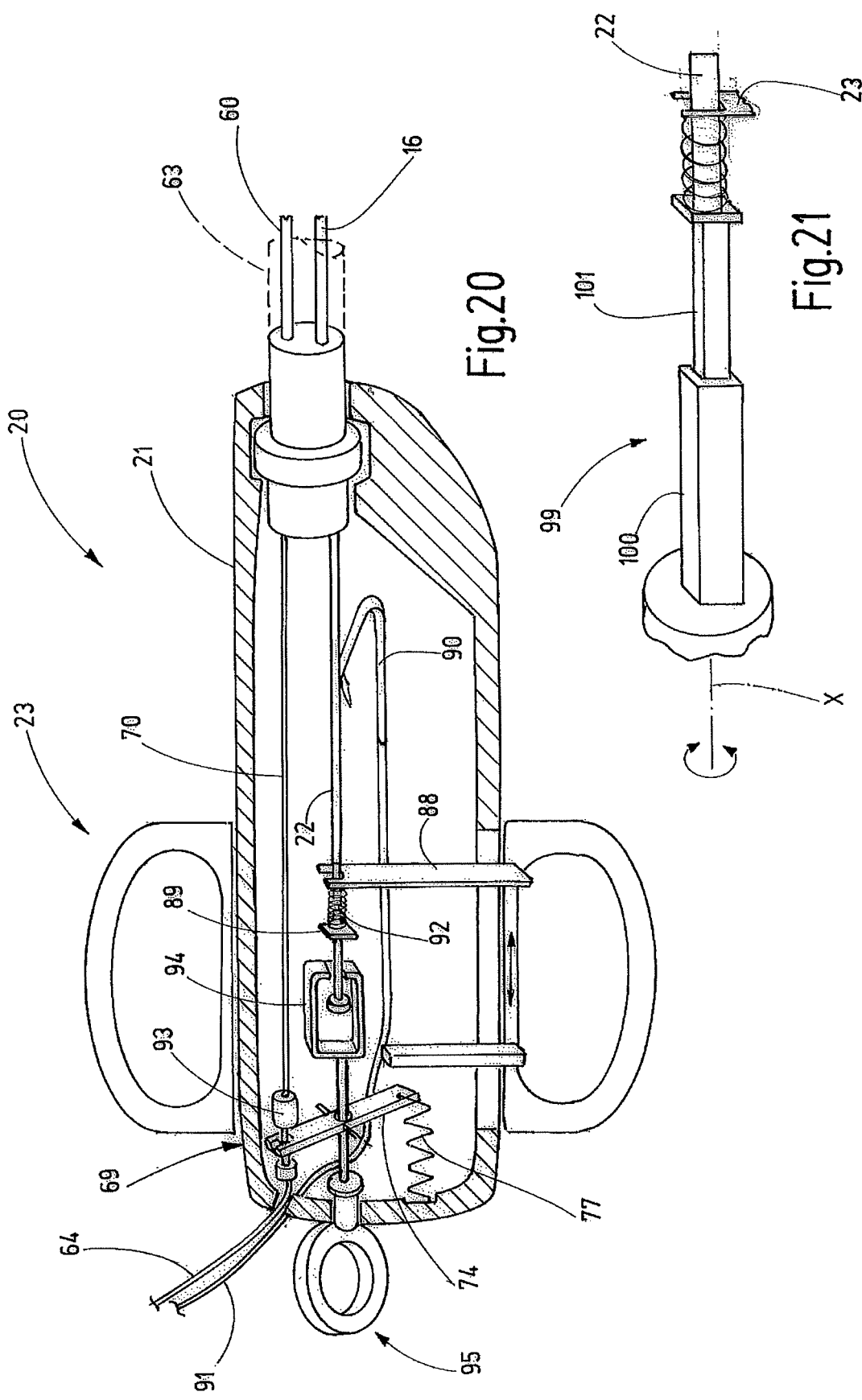

The sliding blocks 31, 32 can be formed by pins or other projections. The lever 27 can also be coupled with the electrode 16 and the electrode operating element 23 in another manner that allows a movement of the coupling locations along the lever 27, if it is pivoted, e.g. a coupling with the lever, as schematically illustrated in FIG. 20.

Instead of the preferred lever gear 26, also other reduction gears 25 can be used, e.g. rack-pinion-gears, toothed wheel gears, spur gears, friction wheel gears, belt gears and the like. The lever gear 26 illustrated here is preferred, due to the simple configuration.

Figures 8, 9:
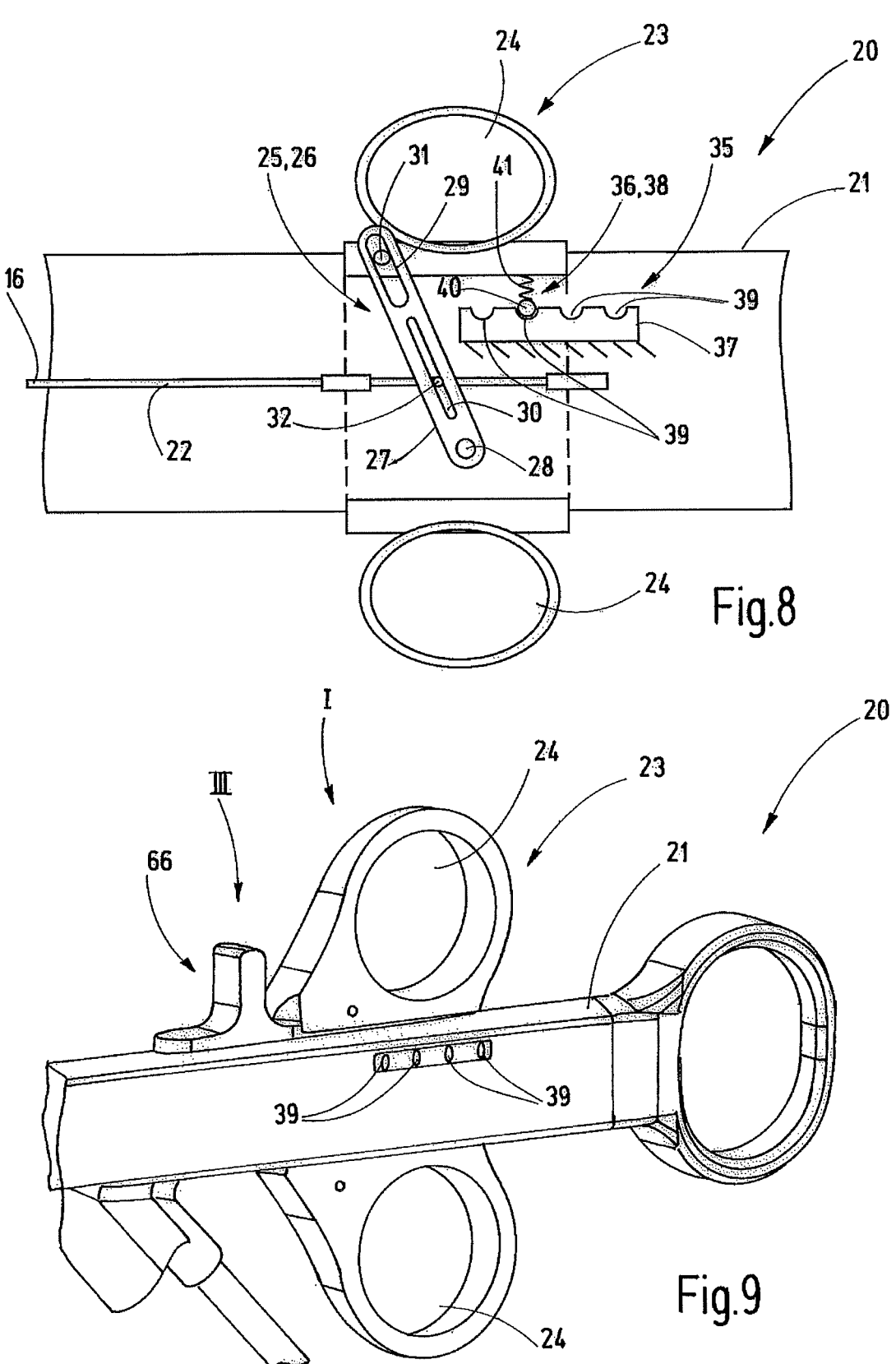

A configuration of the operating device 20 with a latch device 35 is illustrated schematically in FIGS. 8 and 9. The latch device 35 is configured to pre-specify defined positions of the electrode 16 relative to the probe body 12 by multiple different latched positions. Due to the movement coupling of the electrode operating element 23 with the electrode 16 via the reduction gear 25, the latch device 35 can act either directly between the proximal end section 22 of the electrode 16 and the housing 21 or—as in the embodiment—between the electrode operating element 23 and the housing 21. Alternatively, the latch device 35 could also cooperate with any other component of the reduction gear 25 on one hand and the housing 21 on the other hand.

In the embodiment the latch device 35 comprises a latch element 36 that is arranged at the electrode operating element 23 immovably relative to the electrode operating element 23. The latch element 36 cooperates with a latch counter element 37 in order to pre-specify different latched positions according to the defined positions of the electrode 16. The latch counter element is arranged at the housing 21 immovably relative to the housing 21 according to the example.

In the embodiment the latch element 36 comprises at least one latch projection 38 and the latch counter element 37 comprises a latch recess 39. Conversely, also the latch element 36 could comprise at least one latch recess 39 and the latch counter element 37 could comprise a latch projection 38.

In the embodiment illustrated here the latch element 36 is formed by one single latch projection 38. The latch projection 38 comprises a latch body 40, e.g. a latch ball, as well as an elastic support 41 for the latch body 40. For example, a spring and particularly a helical spring can be used as elastic support 41 that is supported on one hand at the electrode operating element 23 and on the other hand supports the latch body 40 or the latch ball. Due to the elastic support 41 the latch body 40 can engage in the latch recess 39 under an elastic biasing force and can be moved against the elastic force of the elastic support 41 out of the latch recess 39 during a relative movement between the latch element 36 and the latch counter element 37. Thus, the latched positions are releasable and a relative movement of the electrode operating element 23 relative to the housing 21 is not excessively impeded or blocked by the latch device 35. For this the shape and depth of the latch recesses 39 can be selected accordingly.

In the embodiment of the latch device 35 illustrated here, one latched position defines the fully extended position A of the electrode 16, whereas another latched position characterizes the fully retracted position E of the electrode 16. Between these two latched positions at least one additional latched position is defined that respectively characterizes an intermediate position of the electrode 16 between the fully extended position A and the fully retracted position E. For example, three, four or more latched positions can be defined by the latch device 35 and thus a respective number of positions of the electrode 16.

The latch device 35 gives haptic feedback to the surgeon during handling of the probe 10 how far the distal end 17 of the electrode 16 is moved out of the probe body 12. This information is at least of importance for the surgeon during some surgical applications. In addition or as an alternative, one or more marks can be provided, e.g. at the housing 21 that indicate the position of the operating element 23 to the surgeon and thus how far the distal end 17 of the electrode 16 projects out of the probe body 12.

As schematically illustrated in FIG. 1, the probe 10 is configured for electrosurgical treatment of tissue 44 by use of the electrode 16 and shall thereby particularly only advance thus far in the tissue 44 that a defined outer tissue layer 45 is separated by the electrode 16. The electrode 16 thereby serves as cutting instrument. The distal end 17 of the electrode 16 is not visible for the surgeon and is located within the tissue 44. For this reason it is important and advantageous for the surgeon, if he is aware of the distance of the distal end 17 of the electrode 16 from the distal end 13 of the probe body 12. Hereby the defined latched positions are helpful.

As schematically illustrated in FIG. 9, the latch counter element 37 can be a strip-shaped element with holes of defined dimension that form a latch recess 39 in each case, for example.

In one embodiment of the probe 10 a biasing device 48 with at least one biasing element 49 can be present in order to apply a biasing force F in extension direction R on the electrode 16 (FIGS. 15-18). The at least one biasing element 49 can be, for example, a spring, particularly a helical spring. In the embodiments illustrated in FIGS. 15-17 the at least one biasing element 49 is arranged inside the electrode channel 15 of the probe body 12. In these embodiments the at least one biasing element 49 applies a force F on the electrode 16 that urges the electrode 16 in the fully extended position A. For this the at least one biasing element 49 and according to the example the helical spring is supported on one side on a first support part 50 and on the other side at a second support part 51. The first support part 50 is arranged at the electrode 16 immovably relative to the electrode 16 and can be formed, e.g. by a flange, ring body or the like. The second support part 51 is arranged at the probe body 12 immovably relative to the probe body 12 and can be, for example, a hollow cylindrical body that provides a through channel for the electrode 16 at the inside and is arranged in the electrode channel 15 of the probe body 12. The at least one biasing element 49 can thus extend between the two support parts 50, 51 and effectuate a biasing force F between the probe body 12 and the electrode 16.

Figures 15, 16, 17, 18:
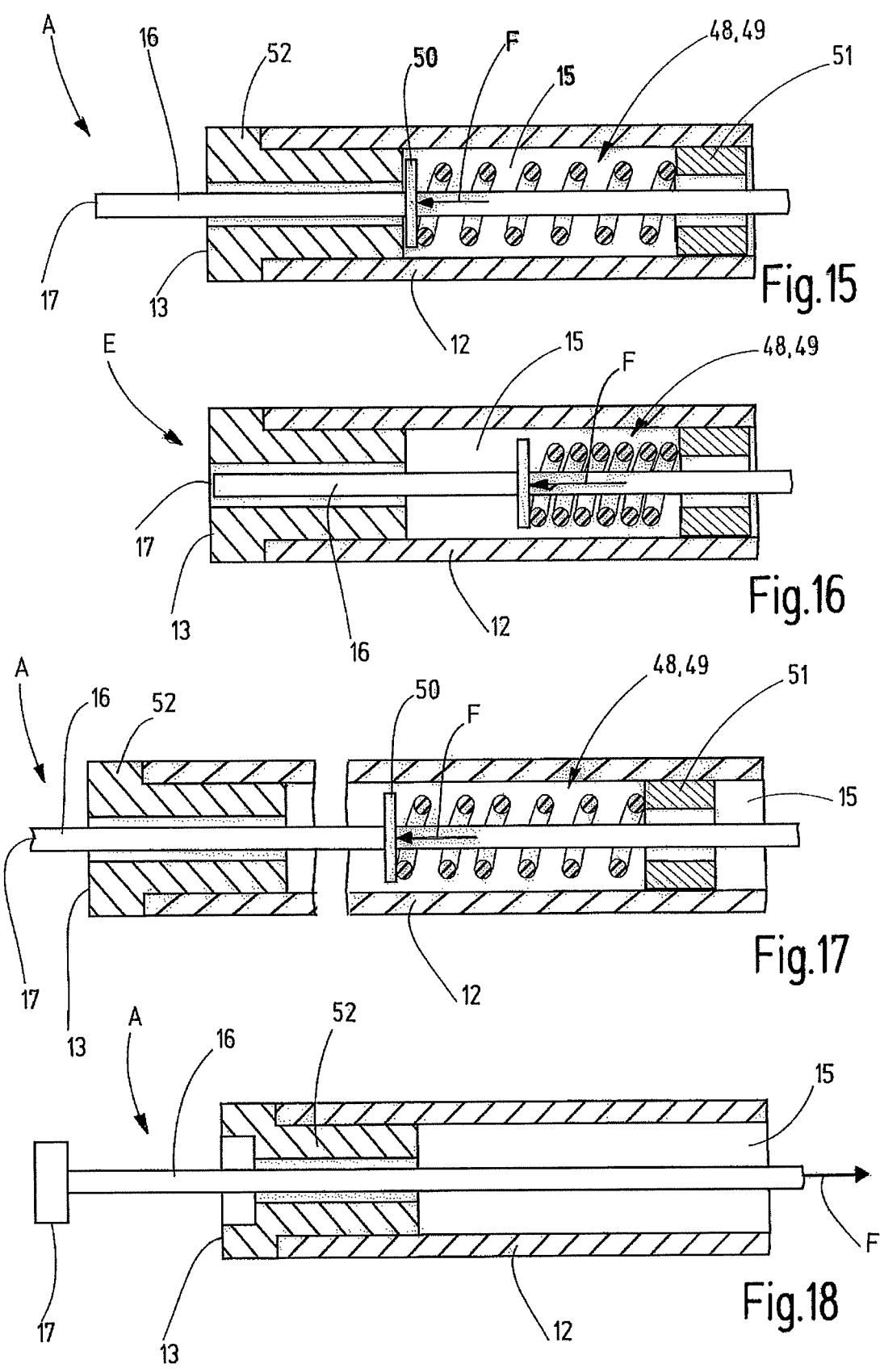

As shown in FIGS. 15 and 16, the at least one biasing element 49 can be arranged directly adjacent to an end piece 52 of the probe body 12. The end piece 52 can be, for example, a ceramic end piece that protects the probe body 12 from sparks and light creation, if voltage is applied to the electrode 16. In the fully extended position A of the electrode 16 the first support part 50 can abut against an inner end of the end piece 52. Such an abutment is, however, not necessarily required, as illustrated based on the example in FIG. 17.

In the embodiment illustrated in FIGS. 15 and 16 the at least one biasing element 49 is positioned directly adjacent to the end piece 52, preferably in an area having a length of 10 mm to 20 mm adjoining the end piece 52 inside the electrode channel 15. In the embodiment illustrated in FIG. 17 the at least one biasing element 49 is arranged with distance to the end piece 52 or the distal end 13 of the probe body that is longer than in the embodiment according to FIGS. 15 and 16. For example, the at least one biasing element 49 can have a distance of 10-15 cm from the end piece 52 or the distal end 13 of the probe body 12. Basically the at least one biasing element 49 can be arranged at an arbitrary location inside the probe body 12, wherein areas near the proximal end 14 or the distal end 13 are preferred, in order to be able to arrange the at least one biasing element 49 or the second support part 51 as simply as possible inside the probe body 12.

Figure 19:
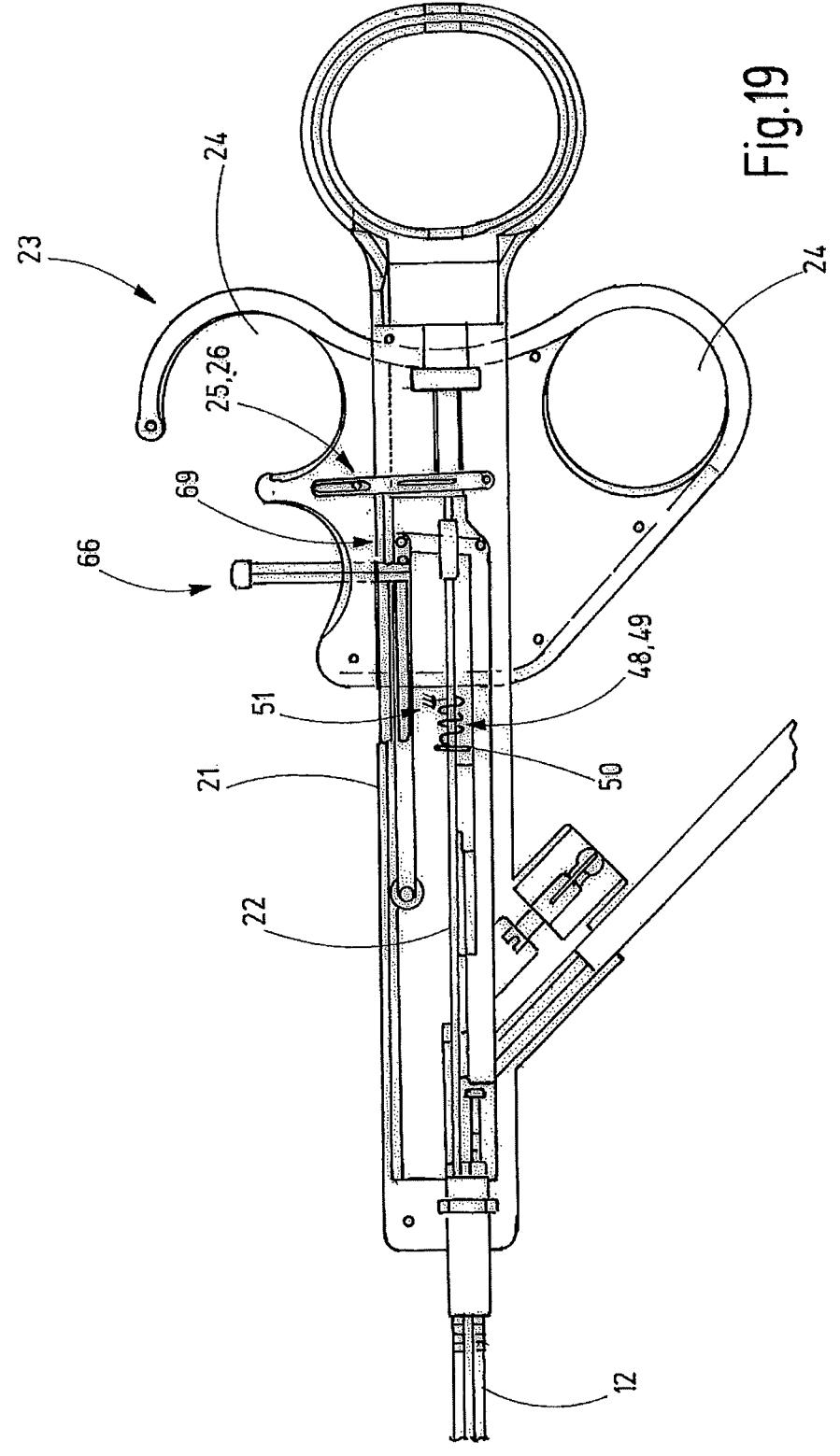

In modification to the embodiments according to FIGS. 15-17 illustrated so far, the biasing device 48 or the at least one biasing element 49 can also be arranged outside the probe body 12 and particularly inside the housing 21, as it is only highly schematically shown in FIG. 19 by way of example. The second support part 51 at which the at least one biasing element 49 is supported thereby is in this arrangement connected with the housing 21 immovably relative to the housing 21.

In modification to the embodiments illustrated so far, the biasing device 48 can also effectuate a biasing force F on the electrode 16 that urges the electrode 16 in direction toward its fully retracted position E, which is as an example illustrated in FIG. 18. In this embodiment the at least one biasing element 49 can urge the distal end 17 of the electrode 16 in direction toward the distal end 13 of the probe body 12 (push or pull). Also springs or helical springs and arrangement can be used here analog to the illustrations according to FIG. 15-17 or 19, wherein for example the second support part 51 can be arranged on the side of the first support part 50 that is closer to the distal end 17 of the electrode 16. Alternatively, the at least one biasing element 49 could also be attached at the support parts 50, 51 and effectuate a tensile force in that it urges the two support parts 50, 51 toward each other and not away from each other, as in the embodiments described so far.

The probe 10 according to the present embodiment is a combined probe or hybrid probe that comprises in addition to the electrode 16 for the electrosurgical treatment a water jet probe body 60 that extends from a proximal end 61 to a distal end 62. In the embodiment the water jet probe body 60 and the electrode 16 can also be arranged in a common outer body 63 that can be formed, e.g. by the probe body 12 and can provide a lumen or a channel for the water jet probe body 60 as well as the electrode 16 respectively.

The water jet probe body 60 comprises a water channel that extends up to the distal end 62. The water channel is fluidically connectable with a water reservoir or a water pressure source, e.g. via a supply line 64. At the distal end 62 of the water jet probe body 60 a water jet can be emitted. By means of the water jet an outer tissue layer 45 can be sub-injected, for example, such that a liquid cushion 65 is formed below the outer tissue layer 45 that separates the outer tissue layer 45 from lower tissue layers of the tissue 44 and simplifies the dissection of an area, particularly a pathological modified area of the outer tissue layer 45 (FIG. 1).

The water jet probe body is shiftably arranged relative to the housing 21 in its extension direction R by means of the operating device 20. Analog to the electrode 16 the position of the distal end 62 of the water jet probe body 60 can be varied in extension direction R. In the embodiment the extension direction R of the electrode 16 and the extension direction R of the water jet probe body 60 are at least substantially parallel in the section that adjoins to the respective distal ends 17 or 62.

In one inventive aspect that can be realized independent from other inventive aspects, the operating device 20 is configured to allow the movement of the water jet probe body 60 in extension direction R toward the extended position, only if the electrode 16 is not in the fully extended position A or preferably if the electrode 16 is in the fully retracted position E.

In the embodiment illustrated in FIGS. 2 and 3 the operating device 20 comprises a water jet probe operating element 66 for shifting the water jet probe body 60. The water jet probe operating element 66 is arranged adjacent to the electrode operating element 23. The water jet probe operating element 66 takes an initial position III, if the water jet probe body 60 is in its retracted position (FIG. 1). The initial position III of the water jet probe operating element 66 is illustrated in FIGS. 2 and 3.

In the embodiment the water jet probe operating element 66 is linearly shiftably supported on the housing 21 in a direction parallel to the shifting direction of the electrode operating element 23. If the electrode operating element 23 takes its first position I, it forms a stop for the water jet probe operating element 66 in its initial position III. If the electrode 16 is thus in its fully extended position A, the water jet probe operating element 66 cannot be moved out of the initial position III. This situation is shown in FIG. 2.

Only if the electrode operating element 23 is moved out of the first position I, e.g. in the second position II, a movement clearance for the water jet probe operating element 66 is provided thereby in order to move it out of the initial position III and thus the water jet probe body 60 out of the retracted position in an extended position (FIG. 3). Thus, in the embodiment of the operating device 20 illustrated in FIGS. 2 and 3 the water jet probe body 60 can be extended concurrently with the retraction of the electrode 16 or after the retraction of electrode 16.

The expressions "retract" and "extend" refer in this application to the probe body 12 (with reference to the electrode 16) and the common outer body 63 or the housing 21 with reference to the water jet probe body 60.

Figures 4, 5:
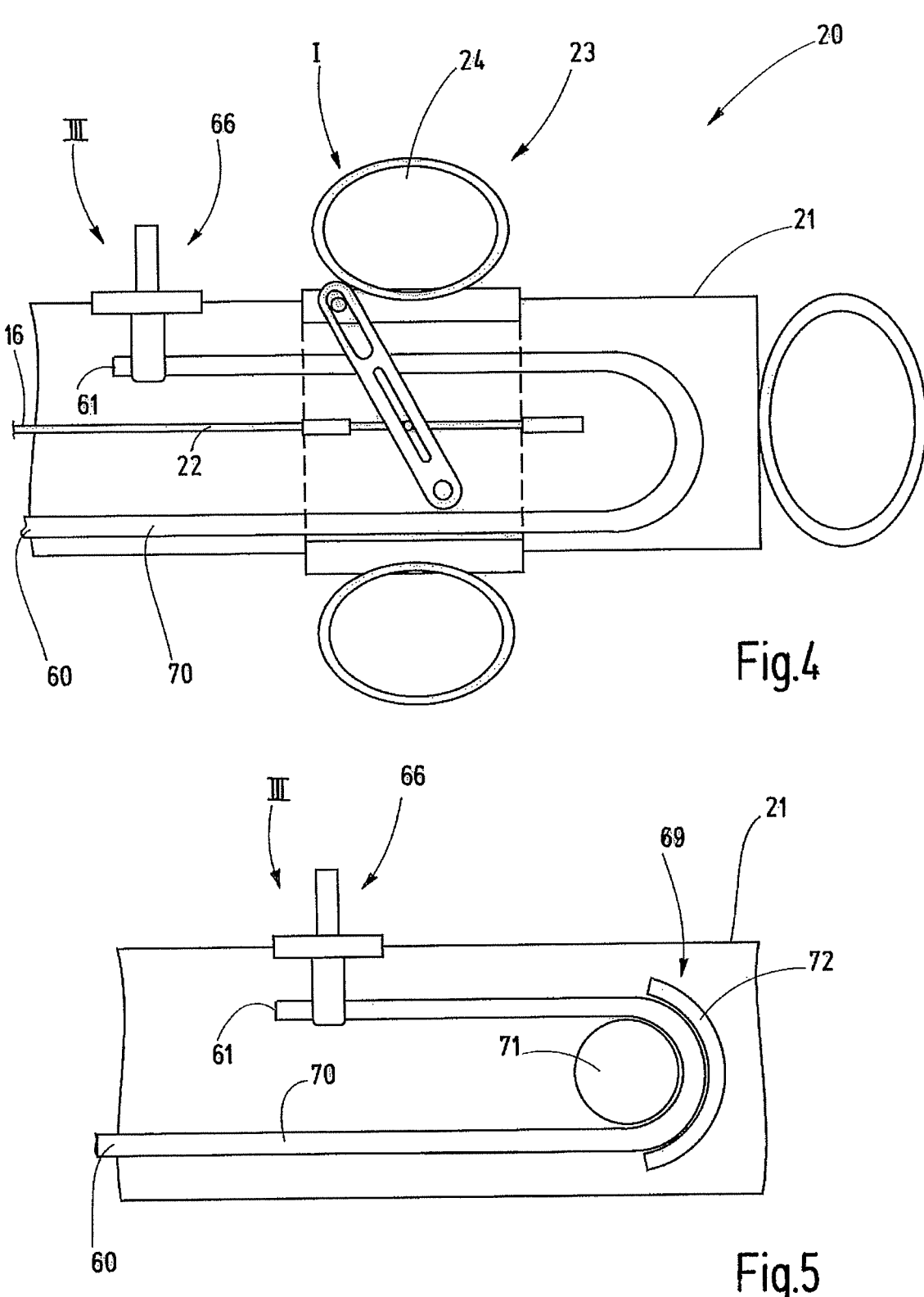

In an alternative embodiment illustrated in FIG. 4 the water jet probe operating element 66 takes the initial position III in a sufficient distance to the electrode operating element 23 in the first position I such that the water jet probe body 60 can be moved independent from the position of the electrode operating element 23 in this embodiment, in order to extend or retract the water jet probe body 60.

Figures 6, 7:
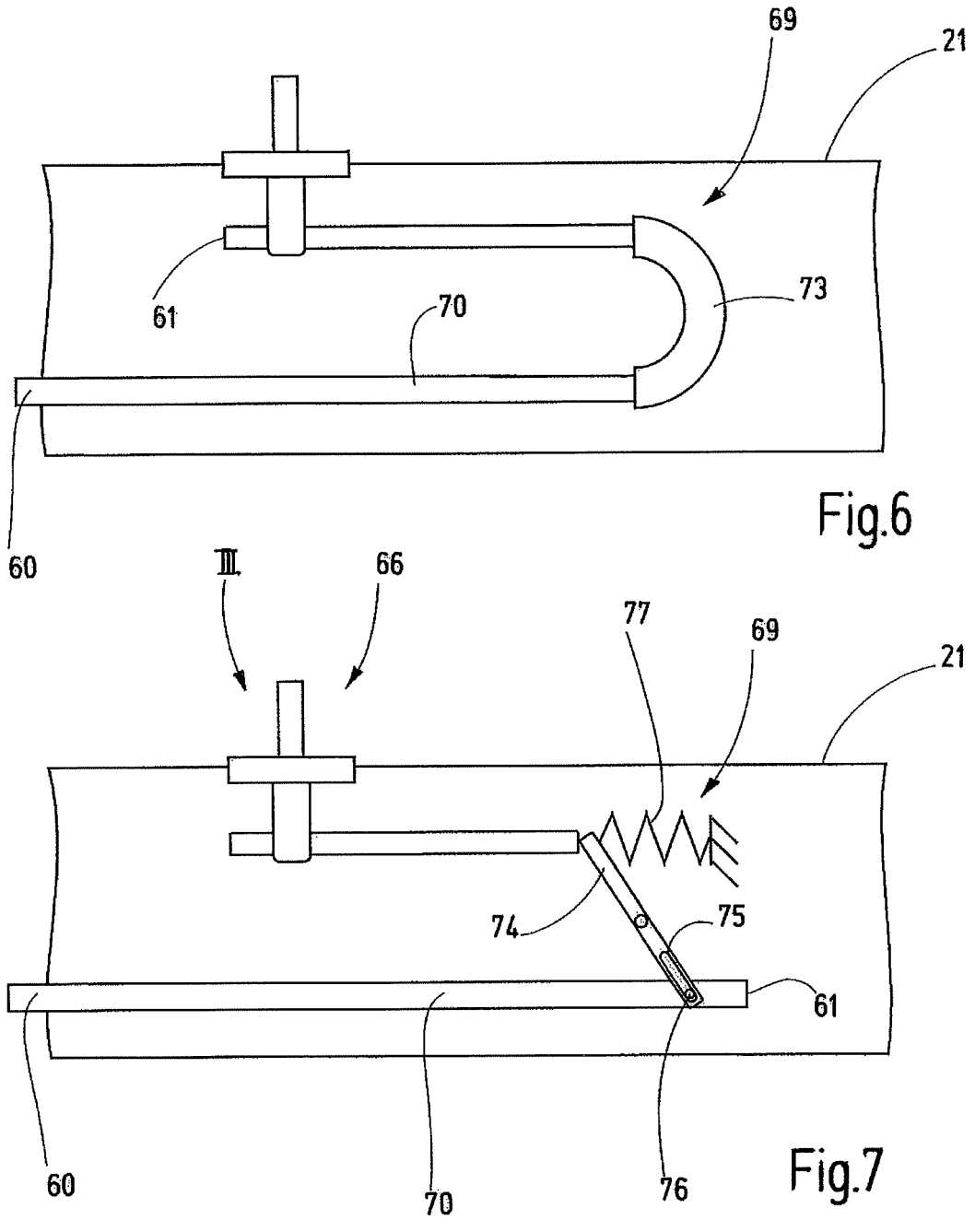

Based on the illustrations in FIGS. 5-7 different possibilities for realizing a deflection device 69 are illustrated. The deflection device 69 arranged in the housing 21 is configured to couple the water jet probe body 60 with the assigned operating element of the operating device 20 such that the movement direction of the water jet probe body 60 arranged outside the housing 21 and the operating element are opposed.

In the embodiments according to FIGS. 5 and 6, the deflection device 69 is configured to deflect or bend a proximal end section 70 of the water jet probe body 60 arranged inside the housing 21 approximately about 180°. For this the deflection device 69 can comprise, e.g. an inner deflection body 71 curved with an inner radius and an outer deflection body 72 curved with an outer radius between which the proximal end section 70 of the water jet probe body 60 extends in a curved guided manner (FIG. 5). Alternatively to this the deflection device 69 can comprise, for example, a curved extending deflection tube 73 through which the proximal end section 70 extends (FIG. 6).

At the proximal end 61 that is located inside the housing 21, the water jet probe body 60 is movably coupled with the water jet probe operating element 66 and is, according to the example, immovably or rigidly connected. Movement of the water jet probe operating element 66 thus leads to a shift of the water jet probe body 60. The sections of the proximal end section 70 extending adjacent to the deflection device 69 thereby move in opposite directions. Thus, by movement of the water jet probe operating element 66 out of the initial position III, an extension movement of the water jet probe body 60 can be initiated, for example, and conversely by a movement of the water jet probe operating element 66 back in direction toward the initial position III, a retraction movement of the water jet probe body 60 can be initiated.

Such an opposed movement can also be effected by another type of deflection device 69, as for example illustrated in FIG. 7. There the deflection device 69 comprises a two-arm lever 74 that is pivotally supported on the housing 21 at the connection location of its two arms and is supported with one arm on the water jet probe operating element 66 and with the other arm at the proximal end section 70 of the water jet probe body 60. The two-arm lever 74 or the water jet probe operating element 66 can be biased by a spring or another elastic or spring elastic unit 77 in the initial position III. The connection between the two-arm lever 74 and the water jet probe body 60 is established by a third groove 75 in the two-arm lever 74 in which a third sliding block 76 engages that is immovably or rigidly arranged at the water jet probe body 60 or its proximal end section 70. Also by means of this two-arm lever 74 an opposed movement can be achieved such that a movement of the water jet probe operating element 66 out of the initial position III leads to an extension movement of the water jet probe body 60 and conversely a movement back into the initial position III effects a retraction movement of the water jet probe body 60.

The transmission ratio of the deflection device 69 according to FIG. 7 between the movement of the water jet probe operating element 66 and the movement of the water jet probe body 60 can be equal to one and alternatively selectively also smaller than one or larger than one. For example, the transmission ratio can be selected by the length of the two arms of the two-arm lever 74.

In the embodiment of the deflection device 69 according to FIG. 7, an embodiment of the operating device 20 can be realized in which a separate water jet probe operating element 66 can be omitted. Thereby one single operating element and, according to the example the electrode operating element 23, can be configured to move the electrode 16 as well as to move the water jet probe body 60.

Figures 10, 11:
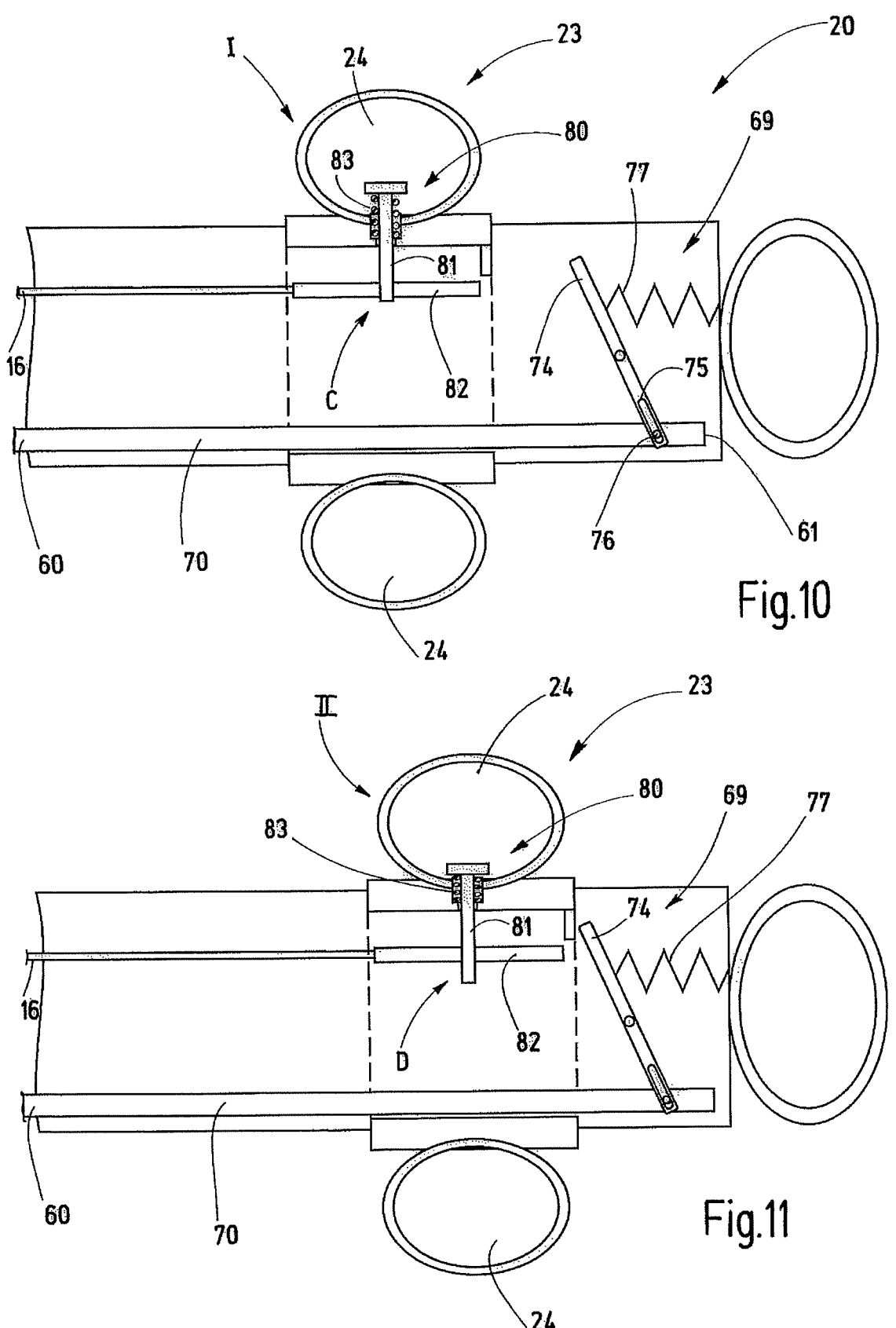
Figures 12, 13, 14:
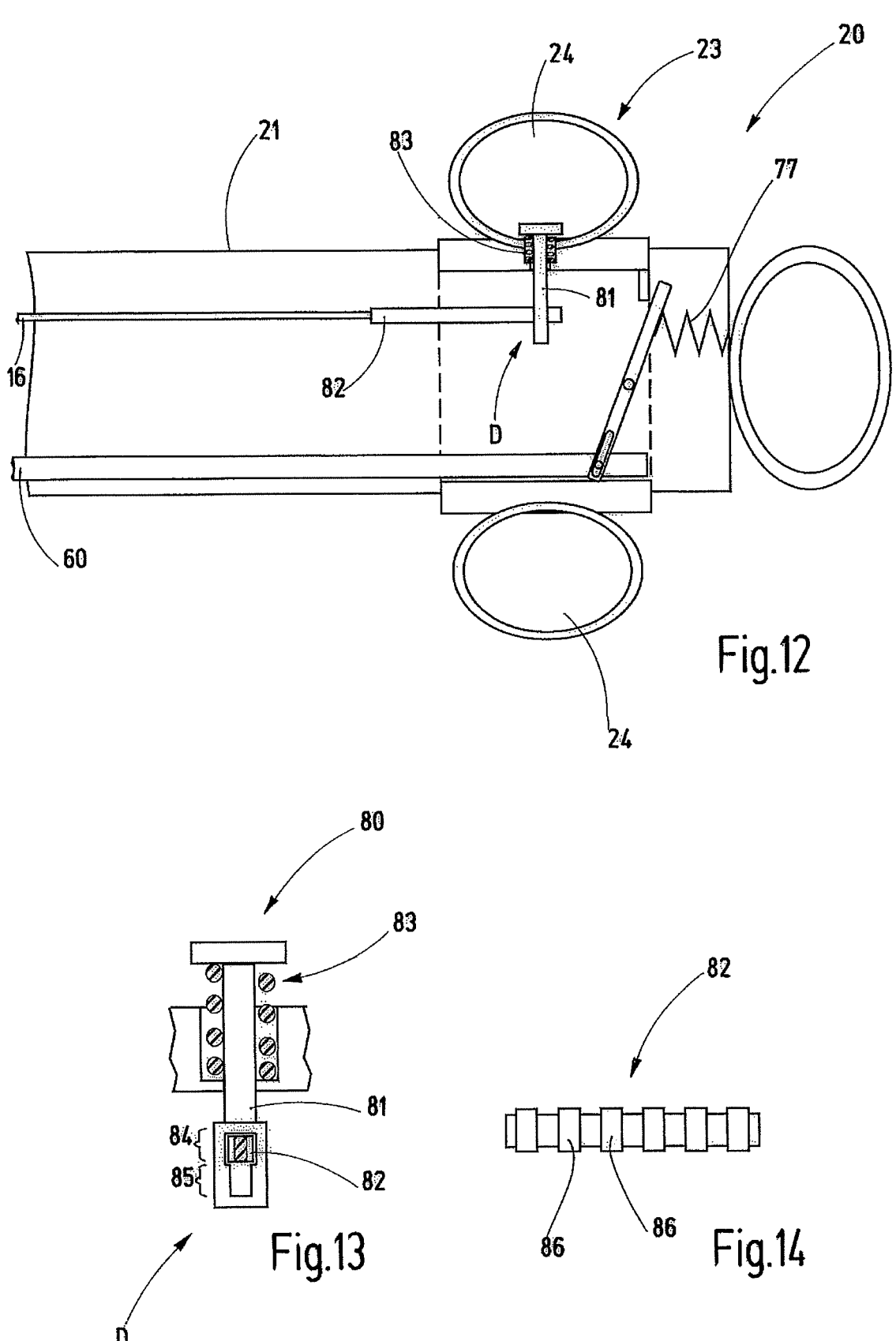

In the embodiment illustrated in FIGS. 10-12 a coupling device 80 is provided by means of which a movement coupling between the electrode operating element 23 and the electrode 16 can be established and disconnected. The coupling device 80 can be configured for manual actuation. In a coupling position C a movement coupling between electrode 16 and the electrode operating element 23 (FIG. 10) exists and in a decoupling position D the movement coupling between the electrode operating element 23 and the electrode 16 is disabled (FIGS. 11 and 12). In the coupling position C a force-fit and/or form-fit connection can be established between an operable coupling part 81 and a coupling body 82 immovably or rigidly connected with the electrode 16, whereas this force-fit and/or form-fit connection is suspended in the decoupling position D, e.g. due to modified position of the coupling part 81. By an elastic or spring elastic element 83 the coupling part 81 can be urged in the coupling position C. The spring elastic element 83 can be, e.g. a helical spring that is supported on one side on the coupling part 81 and the other side on the electrode operating element 23.

By means of the electrode operating element 23 the electrode 16 can be first moved out of the extended position A in direction toward the retracted position E in that the electrode operating element 23 is moved out of the first position I in direction toward the second position II (FIG. 10). During this movement the electrode 16 is retracted. Preferably the electrode 16 has reached its fully retracted position E before the electrode operating element 23 gets in contact with the deflection device 69 and, according to the example the two-arm lever 74. The electrode operating element 23 can thus take the second position II before an extension movement of the water jet probe body 60 is effected by the deflection device 69. Because the electrode 16 is already completely retracted, the coupling device 80 is switched in the decoupling position D in the second position II of the electrode operating element 23 such that a further movement of the electrode operating element 23 is possible. During this continued movement away from the first position I beyond the second position II, the electrode operating element 23 gets in contact with the deflection device 69 and according to the example the two-arm lever 74 and in so doing initiates an extension movement of the water jet probe body 60 (FIG. 12).

The retraction movement of the water jet probe body 60 or the extension movement of the electrode 16 are carried out accordingly in opposite sequence. In the embodiment the water jet probe body 60 is urged by the elastic or spring elastic unit 77 of the deflection device 69 in the retracted position and takes it as soon as the electrode operating element 23 is no longer in contact with the deflection device 69 or reaches the second position II (FIG. 11). Subsequently, the movement coupling between the electrode 16 and the electrode operating element 23 via the coupling device 80 can be re-established such that an extension of the electrode 16 is possible during continued movement from the second position II in the first position I.

According to the example, an embodiment of the coupling device 80 or the coupling body 82 is illustrated in FIGS. 13 and 14 in which a form-fit connection between the coupling part 81 and the coupling body 82 can be established. For this the coupling part 81 has a through opening with a first section 84 and a second section 85. The dimensions of the first section 84 are so large that no force-fit or form-fit connection is established between the coupling body 82 and the coupling part 81. The second section 85 is narrower than the first section 84 and can engage between two fins 86 or enlarged sections of the coupling body 82 and between these two fins 86 create a form-fit connection between the coupling part 81 and the coupling body 82, if the coupling device 80 takes the coupling position C.

In the cross-section illustrated in FIG. 13 the coupling body 82 is in the first section 84 of the through hole so that the coupling device 80 takes the decoupling position D. Due to a movement of the coupling part 81, the second section 85 can be brought to the level of the coupling body 82 (on top in FIG. 13) for switching in the coupling position C in order to create a form-fit and/or force-fit coupling.

FIG. 19 illustrates an embodiment of the operating device 20 in which the water jet probe operating element 66 is movably coupled with the water jet probe body 60 via the deflection device 69. The deflection device 69 can be configured according to the embodiment of FIG. 7. The electrode operating element 23 is coupled with the electrode 16 via a reduction gear 25 and according to the example a lever gear according to FIGS. 2-4.

A further embodiment of the operating device 20 is illustrated in FIG. 20 in which the electrode operating element 23 is configured for moving the electrode 16, as well as for moving the water jet probe body 60. To supply an electrical voltage or an electrical current, a contact spring 90 abuts at the proximal end section 22 of the electrode 16 that can be electrically connected with a voltage and/or current source via an electrical line 91. Such contacting can also be used in all other embodiments of the probe 10.

The electrode operating element 23 is movably coupled with the proximal end section 22 of the electrode 16 via an elastic or spring elastic connection element 92. For this the electrode operating element 23 abuts at the connection element 92, e.g. by means of a transverse part 88 extending into the housing 21, wherein the connection element 92 is supported on the opposite side on a stop part 89 that is immovably connected with the proximal end section 22 of the electrode 16. The connection element 92 can be formed by a helical spring or the like.

In addition, the deflection device 69 is present in the inside of the housing 29 in order to transfer the movement of the electrode operating element 23 in a movement of the water jet probe body 60. The deflection device 69 and the operation of the water jet probe body 60 by means of the electrode operating element 23 corresponds to the embodiments according to FIGS. 10-12 such that reference can be made to the explanations above. Also in the embodiment according to FIG. 20, the electrode 16 is first retracted before an extension movement of the water jet probe body 60 takes place or vice versa.

Instead of the third groove 75 and the third sliding block 76, the lever 74 comprises a slit in the embodiment according to FIG. 20 through which the proximal end section 70 of the water jet probe body 60 extends. Adjoining the slit a stop body 93 is connected with the proximal end section 70 immovably relative to the proximal end section 70, wherein the dimensions of the stop body 93 are larger than those of the slit in the two-arm lever 74. Also in this configuration the two-arm lever 74 can initiate a movement of the water jet probe body 60 via the stop body 93.

In the embodiment according to FIG. 20, the elastically deformable connection element 92 is present instead of the coupling device 80. As soon as the electrode operating element 23 takes the second position II in which the electrode 16 is fully retracted, the connection element 92 is elastically deformed and allows thereby a continued movement of the electrode operating element 23 in order to carry out the movement of the water jet probe body 60 due to contact with the deflection device 69. The electrode 16 can abut, for example, at a part of the housing 21 or the probe body 12—for example the stop part 89 can abut at the counter stop 94 and/or an enlarged distal end 17 can abut at an end piece 52 (FIG. 18)—the further retraction movement of electrode 16 is stopped and the continued movement of the electrode operating element 23 leads to an elastic deformation of the connection element 92. In the movement range between the first position I and the second position II of the electrode operating element 23 the water jet probe body 60 remains in the retracted position and only the electrode 16 is retracted or extended.

As an option and depending on the configuration of the electrode 16, an adjustable counter stop 94 can be provided for the stop part 89. By means of the position of the counter stop 94 the second position II can be defined. As soon as the electrode 16 abuts at a stop—for example the stop part 89 at the counter stop 94 and/or an enlarged distal end 17 at an end piece 52 (FIG. 18)—a further retraction movement of the electrode 16 is stopped and continued movement of the electrode operating element 23 leads to an elastic deformation of the connection element 92. For adjustment of the position of the counter stop 94 a rotatable adjustment screw 95 can be provided, for example, that is coupled with the counter stop 94 via a threaded connection and varies the position of the counter stop 94 parallel to the movement direction of the electrode operating element 23 during rotation.

FIG. 21 illustrates a further optional configuration of the operating device 20 that in addition illustrates a rotary mechanism 99 in order to be able to rotate the electrode 16 about its own longitudinal axis or extension axis, e.g. if the distal end 17 of the electrode 16 is configured in a non-rotational symmetric manner. The rotary mechanism 99 can comprise a preferably non-round rotary part 100 rotatable about a rotary axis X, e.g. tube having a non-circular inner cross-section, and a preferably non-round telescopic part 100, e.g. an insertion part. The rotary part 100 and the telescopic part 101 are telescopically shiftable and torque-proof connected with each other. For example, the telescopic part 101 is insertable into a non-circular rotary part 100, wherein the cross-section of the telescopic part 101 can correspond substantially to the inner cross-section of the tube-shaped rotary part 100. During rotation of the tube-shaped rotary part 100 about the rotary axis X the telescopic part 101 also rotates about the rotary axis X. The telescopic part 101 is in turn torque-proof connected with the electrode 16 or the proximal end section 22.

The rotary part 100 and/or the telescopic part 101 can be telescopically shiftably arranged parallel to the rotary axis X or along the rotary axis X in order to be able to extend and retract the electrode 16. The rotary part 100 can be connected with an operating element on the housing 21 that is accessible from outside in a torque-proof or operational manner.

One aspect of the invention refers to a probe 10 for electrosurgical treatment of tissue 44. In a probe body 12 an electrode 16 is movably arranged in an extension direction R of an electrode channel 15. The probe body 12 is connected with an operating device 20 at the proximal end 14. It comprises an electrode operating element 23 to shift the electrode 16 along the electrode channel 15. The movement coupling between the electrode operating element 23 and the electrode 16 is established via a reduction gear 25, e.g. a lever gear 26. In another independent aspect of the invention a latch device 35 is provided that defines two, three or more releasable latched positions that correspond to a pre-defined position of the electrode 16 relative to the probe body 12 in each case. Another independent inventive aspect is that the probe 10 is configured as combined probe or hybrid probe and comprises a water jet probe body 60 that extends substantially parallel to the probe body 12 and is movable or shiftable in extension direction R by the operating device 20. In doing so, the operating device 20 can be configured such that an extension movement of the water jet probe body is only possible, if the electrode 16 is retracted or already takes the fully retracted position E.

The invention claimed is:

1. A probe for electrosurgical treatment of tissue, the probe comprising:
   a probe body in which an electrode channel extends up to a distal end of the probe body;
   an operating device comprising a housing, wherein the operating device is connected with a proximal end of the probe body and the operating device comprises an electrode operating element on the housing that is movable between a fully extended position, a fully retracted position, and at least one intermediate position between the fully extended position and the fully retracted position;
   an electrode configured to be shiftable in the electrode channel in an extension direction of the electrode channel, and movably coupled with the electrode operating element; and
   a water jet probe body in which a water channel extends up to a distal end of the water jet probe body, wherein the water jet probe body is shiftable along a movement path in its extension direction relative to the housing of the operating device, wherein the operating device is configured to allow a movement of the water jet probe body in a direction toward an extended position, wherein the operating device comprises a water jet probe operating element that is movably coupled with the water jet probe body and is configured to shift the water jet probe body in its extension direction relative to the housing of the operating device, wherein the electrode operating element is configured to function as a mechanical stop for the water jet probe operating element only when the electrode operating element is in the fully extended position, such that the water jet probe operating element is movable in its extension direction along the movement path toward its extended position when the electrode operating element is in the at least one intermediate position and when the electrode operating element is in the fully retracted position, and wherein the electrode operating element is arranged in the movement path of the water jet probe operating element to form the mechanical stop for the water jet probe operating element, in order to block the movement of the water jet probe operating element when the electrode operating element is in the fully extended position, and the electrode operating element is moveable between the fully extended position and the fully retracted position, and the fully retracted position and the fully extended position, without moving the water jet probe body in its extension direction, wherein the water jet probe operating element is linearly movably supported on the housing along a common linear axis with the electrode operating element.

2. The probe according to claim 1, wherein the electrode is movably coupled with the electrode operating element via a reduction gear such that a travelled operating path of the electrode operating element is larger than a path that the electrode travels in the electrode channel.

3. The probe according to claim 2, wherein the reduction gear is a lever gear and wherein the lever gear comprises a lever that is pivotably supported on the housing of the operating device at a pivot location, wherein a coupling location between the lever and the electrode operating element is farther away from the pivot location than a coupling location between the lever and the electrode.

4. The probe according to claim 1, further comprising a latch device configured to define different positions of the electrode relative to the probe body by one latched position in each case.

5. The probe according to claim 4, wherein the latch device defines a fully extended position of the electrode, a fully retracted position of the electrode and at least one intermediate position of the electrode between the fully extended position and the fully retracted position.

6. The probe according to claim 4, wherein the latch device comprises a latch element movably coupled with the electrode operating element and a latch counter element movably coupled with the housing that provide a releasable latched connection in multiple different relative positions.

7. The probe according to claim 6, wherein the latch element comprises at least one latch projection and the latch counter element comprises multiple latch recesses.

8. The probe according to claim 6, wherein the latch element comprises multiple latch projections and the latch counter element comprises at least one latch recess.

9. The probe according to claim 1, further comprising a biasing device configured to apply a biasing force on the electrode relative to the probe body in an extension direction.

10. The probe according to claim 9, wherein the biasing force of the biasing device urges the electrode in a direction toward a fully extended position.

11. The probe according to claim 9, wherein the biasing device is arranged in the probe body and/or the housing.

12. The probe according to claim 1, wherein the electrode operating element jointly includes the water jet probe operating element and the electrode operating element and the electrode operating element is configured to move the electrode and the water jet probe body.

13. The probe according to claim 12, wherein the electrode operating element is configured to cause a retraction movement of the electrode and then cause an extension movement of the water jet probe body during a movement from the fully extended position in a direction toward the at least one intermediate position or the fully retracted position.

14. The probe according to claim 1, further comprising a deflection device arranged in the housing and configured to couple the water jet probe body with an assigned operating element of the operating device such that a first movement direction of the water jet probe body arranged outside the housing and a second movement direction of the operating element are opposite to each other.

\* \* \* \* \*